United States Patent
Fleischmann (10) Patent No.: US 9,271,730 B2
(45) Date of Patent: Mar. 1, 2016

(54) INSTRUMENT FOR STRETCHING THE SKIN

(76) Inventor: Wilhelm Fleischmann, Freiburg i. Br. (DE)

(*) Notice: Subject to any disclaimer, the term of this patent is extended or adjusted under 35 U.S.C. 154(b) by 231 days.

(21) Appl. No.: 13/995,092

(22) PCT Filed: Nov. 28, 2011

(86) PCT No.: PCT/EP2011/005959
§ 371 (c)(1),
(2), (4) Date: Jun. 17, 2013

(87) PCT Pub. No.: WO2012/079702
PCT Pub. Date: Jun. 21, 2012

(65) Prior Publication Data
US 2013/0282056 A1    Oct. 24, 2013

(30) Foreign Application Priority Data
Dec. 15, 2010 (DE) .......... 10 2010 054 637

(51) Int. Cl.
*A61B 17/04* (2006.01)
*A61B 17/08* (2006.01)
*A61B 19/00* (2006.01)

(52) U.S. Cl.
CPC ............ *A61B 17/08* (2013.01); *A61B 19/24* (2013.01); *A61B 2017/081* (2013.01)

(58) Field of Classification Search
USPC ........................... 606/216, 217, 218
See application file for complete search history.

(56) References Cited

U.S. PATENT DOCUMENTS

| | | | |
|---|---|---|---|
| 268,632 A | * | 12/1882 | Danforth ............ 606/218 |
| 583,455 A | | 6/1897 | Bush |
| 2,450,194 A | | 9/1948 | Glaser |
| 2,669,747 A | | 2/1954 | Detaranto |
| 3,825,010 A | | 7/1974 | McDonald |
| 3,971,384 A | | 7/1976 | Hasson |
| 4,382,441 A | | 5/1983 | Svedman |
| 4,430,998 A | | 2/1984 | Harvey |

(Continued)

FOREIGN PATENT DOCUMENTS

| | | |
|---|---|---|
| DE | 4335432 | 4/1995 |
| DE | 19832634 | 1/2000 |

(Continued)

OTHER PUBLICATIONS

Keetenwirk-Praxis, "Neue Musterungsmoglichkeiten," 2: 47-48 (2001).

(Continued)

*Primary Examiner* — Tuan V Nguyen
(74) *Attorney, Agent, or Firm* — Akerman LLP; Peter A. Chiabotti (57) ABSTRACT

Instrument for stretching the skin for closing wounds, having a skin expander, having at least two jaws mechanically adjustable relative to each other in a tension direction on the skin expander, having barbs associated with the jaws the barbs being anchorable in the skin in the area of the edges of the wound, wherein a tensile force is exerted on the skin by means of the barbs by adjusting the jaws, the force stretching the skin and drawing the edges of the wound toward each other, wherein one or more barbs are each disposed on a carrier extending transverse to the tension direction, wherein the carriers are releasably mounted on the jaws, and wherein the carriers can be fixed in position relative to each other by attachable fixing elements.

10 Claims, 10 Drawing Sheets

(56) References Cited

U.S. PATENT DOCUMENTS

| | | | |
|---|---|---|---|
| 4,526,173 | A | 7/1985 | Sheehan |
| 4,881,546 | A | 11/1989 | Kaessmann |
| 4,896,680 | A | 1/1990 | Hirshowitz |
| 5,127,412 | A | 7/1992 | Cosmetto |
| 5,176,663 | A | 1/1993 | Svedman et al. |
| 5,203,783 | A | 4/1993 | Harle |
| 5,234,462 | A | 8/1993 | Pavletic |
| 5,263,971 | A | 11/1993 | Hirshowitz |
| 5,291,887 | A | 3/1994 | Stanley et al. |
| 5,441,540 | A | 8/1995 | Kim |
| 5,478,340 | A | 12/1995 | Kluger |
| 5,486,196 | A | 1/1996 | Hirshowitz |
| 5,507,775 | A | 4/1996 | Ger |
| 5,531,790 | A | 7/1996 | Frechet |
| 5,549,640 | A | 8/1996 | Fontenot |
| 5,549,713 | A | 8/1996 | Kim |
| 5,571,138 | A | 11/1996 | Blomqvist |
| 5,584,856 | A | 12/1996 | Jameel |
| 5,589,245 | A | 12/1996 | Roell |
| 5,618,310 | A | 4/1997 | Ger |
| 5,636,643 | A | 6/1997 | Argenta et al. |
| 5,645,081 | A | 7/1997 | Argenta et al. |
| 5,653,699 | A | 8/1997 | Reed et al. |
| 5,662,714 | A | 9/1997 | Charvin |
| 5,723,009 | A | 3/1998 | Frechet |
| 5,733,305 | A | 3/1998 | Fleischmann |
| 5,759,193 | A | 6/1998 | Burbank |
| 5,807,295 | A | 9/1998 | Hutcheon et al. |
| 5,814,067 | A | 9/1998 | Fleischmann |
| 5,893,879 | A | 4/1999 | Hirshowitz |
| 5,928,231 | A | 7/1999 | Klien |
| 6,010,524 | A | 1/2000 | Fleischmann |
| 6,106,544 | A | 8/2000 | Brazeau |
| 6,120,525 | A | 9/2000 | Westcott |
| 6,142,982 | A | 11/2000 | Hunt et al. |
| 6,254,624 | B1 | 7/2001 | Oddsen |
| 6,315,780 | B1 | 11/2001 | Lalonde |
| 6,398,767 | B1 | 6/2002 | Fleischmann |
| 6,471,715 | B1 | 10/2002 | Weiss |
| 6,733,537 | B1 | 5/2004 | Fields |
| 6,755,052 | B1 | 6/2004 | Sytz |
| 6,755,807 | B2 | 6/2004 | Risk et al. |
| 7,208,006 | B2 | 4/2007 | Fleischmann |
| 7,235,090 | B2 | 6/2007 | Buckman |
| 7,520,872 | B2 | 4/2009 | Biggie et al. |
| 8,092,491 | B2 | 1/2012 | Fleischmann |
| 8,114,124 | B2 | 2/2012 | Buckman |
| 8,376,972 | B2 | 2/2013 | Fleischmann |
| 8,430,908 | B2 | 4/2013 | Fleischmann |
| 2002/0188170 | A1 | 12/2002 | Santamore et al. |
| 2003/0163160 | A1 | 8/2003 | O'Malley et al. |
| 2003/0176890 | A1 | 9/2003 | Buckman et al. |
| 2003/0225436 | A1 | 12/2003 | Fleischmann |
| 2004/0267309 | A1 | 12/2004 | Garvin |
| 2005/0209574 | A1 | 9/2005 | Boehringer et al. |
| 2007/0156175 | A1 | 7/2007 | Weadock et al. |
| 2007/0191885 | A1 | 8/2007 | Fleischmann |
| 2008/0147115 | A1 | 6/2008 | O'Malley et al. |
| 2008/0208251 | A1 | 8/2008 | Weadock et al. |
| 2008/0312685 | A1 | 12/2008 | O'Malley et al. |
| 2009/0326578 | A1 | 12/2009 | Ewers et al. |
| 2010/0030260 | A1 | 2/2010 | Fleischmann |

FOREIGN PATENT DOCUMENTS

| | | |
|---|---|---|
| DE | 19844355 | 4/2000 |
| DE | 10209122 | 10/2003 |
| DE | 102007011570 | 9/2008 |
| EP | 271741 | 6/1988 |
| EP | 0617152 | 9/1994 |
| EP | 0880953 | 12/1998 |
| EP | 1340461 | 9/2003 |
| EP | 1131024 | 9/2004 |
| FR | 2756722 | 6/1998 |
| FR | 2758711 | 7/1998 |
| GB | 2292526 | 2/1996 |
| JP | H10-510441 | 10/1998 |
| RU | 2021765 | 10/1994 |
| SU | 848001 | 7/1981 |
| SU | 1371592 | 2/1988 |
| SU | 1412751 | 7/1988 |
| SU | 1424809 | 9/1988 |
| SU | 1457906 | 2/1989 |
| WO | 9309727 | 5/1993 |
| WO | 95/16416 | 6/1995 |
| WO | 9526698 | 10/1995 |
| WO | 9608223 | 3/1996 |
| WO | 96/18345 | 6/1996 |
| WO | 0018343 | 4/2000 |
| WO | 01/93771 | 12/2001 |
| WO | 01/93772 | 12/2001 |
| WO | 02087481 | 11/2002 |
| WO | 2010/092455 | 8/2010 |

OTHER PUBLICATIONS

Wollina et al., "Spacer Fabrics—A Potential Tool in the Prevention of Chronic Wounds," Exog Dermatol, 1: 276-278 (2002).

Melis et al., "Primary skin closure of a large groin defect after inguinal lymphadenectomy for penile cancer . . . ," In: The Jour. of Urology, 159(1): 185-187 (1998).

Hirshowitz et al., "Reconstructions of the tip of the nose and ala by load cycling of the nasal skin and harnessing of extra skin," In: Plast Reconstr Surg, 77:316 (1986).

Patent Cooperation Treaty, "International Search Report" by European Patent Office, Officer Neef, Tatjana in PCT/EP2011/005959, Document of 3 pages, dated Mar. 16, 2012.

State Intellectual Property Office of the P.R.C., "First Office Action," by the Chinese Patent Office Examination Division, in Chinese Patent Application No. 201180058472.7, dated Feb. 2, 2015, document of 8 pages.

Japanese Patent Office, "Notice of Reasons for Rejection," with English-language translation, by the Japanese Patent Office, in Japanese Patent Application No. 2013-543562, issued Aug. 4, 2015, document of 9 pages.

* cited by examiner

INSTRUMENT FOR STRETCHING THE SKIN

CROSS REFERENCE TO RELATED APPLICATIONS

This application is a §371 National Phase of PCT/EP2011/005959, filed Nov. 28, 2011, which claims priority to German Patent Application No. 10 2010 054 637.2, filed Dec. 15, 2010, the entireties of which are incorporated by reference herein.

BACKGROUND

The invention relates to an instrument for stretching the skin for closing wounds.

SUMMARY

In addition to skin transplantation, known methods for closing large areas of skin defects include in particular the so-called skin stretching. In skin stretching, in particular a skin expander or skin distractor is used, having at least two jaws anchored with associated barbs in the wound edges opposite one another. The jaws are moved mechanically relative to one another and toward one another, resulting in a tensile force being exerted on the skin, thereby stretching the skin and pulling the edges of the wound together toward one another. The skin is stretched beyond its natural limit of elasticity by means of a tensile force applied for a defined time period, resulting in additional tissue proliferation such that an increase in surface area of the body's own skin can be achieved in a manner suitable for closing the wound.

Skin expanders suitable for skin stretching are known in many different embodiments. For example, the jaws can be moved toward one another on guides by means of a spindle (e.g. EP 0 797406 B1). Another known method is to use pushers to move the jaws on a toothed latching arrangement that is formed on a flexible strip or a rigid bar (e.g., EP 2 120 767 B1). As is known from this prior art, the barbs that are pierced into the skin at the edges of the wound for anchoring the jaws can be formed onto the jaws themselves or can be inserted into the jaws as barb modules. In the case of skin stretching using the known instruments, the edges of the wound are pulled together, thereby stretching the skin areas adjacent to the wound, in a single step, or in the case of large-area wounds in multiple steps, until the opposite edges of the wound rest against one another and can be stitched together. Thus, the skin expander, which in part is bulky and complex, remains at the wound for an extended period of time, which in some cases can be a few days. In large-area wounds, it can sometimes be necessary to use a plurality of skin expanders next to one another.

The object is to provide an instrument for stretching skin for closing wounds which enables improved wound treatment and is more economical in use.

This object is achieved by an instrument having the features and structures disclosed herein.

Advantageous embodiments of the invention are listed in the dependent claims.

The essential idea of the invention is to dispose each of the barbs to be pierced into the skin at the edges of the wound on a carrier that is mounted removably in the respective jaw of the skin expander. After piercing the barbs into the edges of the wound, the jaws, with the carriers held in the jaws, are moved toward one another by means of the skin expander so as to close the edges of the wound by stretching the skin. When the stretching process by means of the skin expander is finished, the carriers anchored by means of the barbs at the wound edges opposite one another are fixed in their relative position using an attachable fixing element. The skin expander can then be removed from the carriers so that the edges of the wound are now held together by means of the carriers and their barbs, the carriers being connected to one another by means of the fixing elements.

The instrument has important advantages. After the edges of the wound are pulled together and the wound is closed, the carriers fixed to the edges of the wound can be fixed by means of the fixing elements, and the skin expander can be removed. Through the fixed and remaining carriers, the edges of the wound can be held together for an extended period of time so that stitching of the edges of the wound is not required. The removed skin expander can be used for further operations.

In the case of large skin defects, the skin expander can also subsequently be used to laterally connect further carriers with barbs to the first carriers and introduce them in the edges of the wound so as to close the wound in steps. For this, the complex skin expander can be designed as a sterilizable instrument that can be used multiple times.

The fixing elements can be provided in various dimensions in order to hold the carriers, fixed in the wound edges opposing one another, at different relative distances. If the wound can be closed in a single stretching step, fixing elements are used that fix the carriers opposing one another at such a distance that the edges of the wound rest against one another and are held together. If wound closure is not possible in a single stretching step, fixing elements can be used which fixedly hold the carriers opposing one another at a distance appropriate for each of the stretching steps. The skin expander can be removed and used elsewhere until it is used again for the next stretching step at the carriers. Since the carriers and fixing elements remaining at the wound require only small space, the wound, which has not yet been completely closed, can in the meantime be optimally treated until the next use of the skin expander. In particular, the wound can be covered in the meantime by a vacuum seal that is placed over the carriers anchored at the wound edges and over the fixing elements.

In an advantageous embodiment, the carriers are designed as bolts that are disposed transverse to the direction of tension of the skin expander and carry the barbs. The fixing elements can be designed in a simple manner as discs that can be placed on the free ends of the carriers to be fixed opposite one other. The bolts can be placed in a receptacle of the respective jaws, the receptacle running transverse to the direction of tension. These receptacles are open in the direction of tension, i.e., in the direction facing the wound. When using the skin expander, the carriers are held in the respective receptacles by virtue of the elastic tension of the skin. When the carriers opposing one another are held in their position by the fixing elements, the jaws can be moved away from one another so that the carriers can come free from the jaws and the skin expander can be removed.

Preferably, the barbs are formed on barb modules, wherein each barb module comprises only one or a few barbs. The barb modules can be pushed onto the bolts which form the carriers so that the number of barbs and their mutual distance on the carrier, i.e., parallel to the edge of the wound, can be variably selected.

BRIEF DESCRIPTION OF THE DRAWINGS

The invention is explained in more detail below with the aid of the exemplary embodiments depicted in the drawing. In the figures.

DETAILED DESCRIPTION OF THE ILLUSTRATED EMBODIMENTS

The instrument according to the invention for stretching skin comprises a skin expander shown in one embodiment in the drawing. Other embodiments of the skin expander as are known from the prior art can also be used within the context of the invention.

The skin expander comprises an elongated, straight guide bar 10. The guide bar 10 has a non-round, for example a rectangular, cross-section. Longitudinally-moveable jaws 12 are disposed on the guide bar 10. The jaws 12 are longitudinally movable on the guide bar 10, for which purpose the jaws comprise a sleeve-like pusher 14 which is guided on the guide rod 10 by means of an opening 16. The inner cross-section of the opening 16 corresponds to the outer cross-section of the guide bar 10 so that the jaws 12 are non-rotatably guided on the guide bar 10. A toothed latching arrangement 18 is formed in the longitudinal direction of the guide bar 10. A latch lever 20 is pivotably attached to the pusher 14 and engages with a latching tooth 22 in the toothed latching arrangement 18. The toothed latching arrangement 18 is designed such that each of the pushers 14 can be moved from one of the two ends of the guide bar 10 toward the middle of the guide bar 10, wherein the latching tooth 22 slides over the toothed latching arrangement 18 and is elastically deflected thereby. However, the latching tooth 22 that engages in the toothed latching arrangement 18 prevents the pushers 14 from being moved back toward the ends of the guide bar 10. An outward movement of the pushers 14 back toward the ends of the guide bar 10 is only possible when the respective latching tooth 22 is lifted out of the toothed latching arrangement 18 by means of the latch lever 20.

Figure 3:
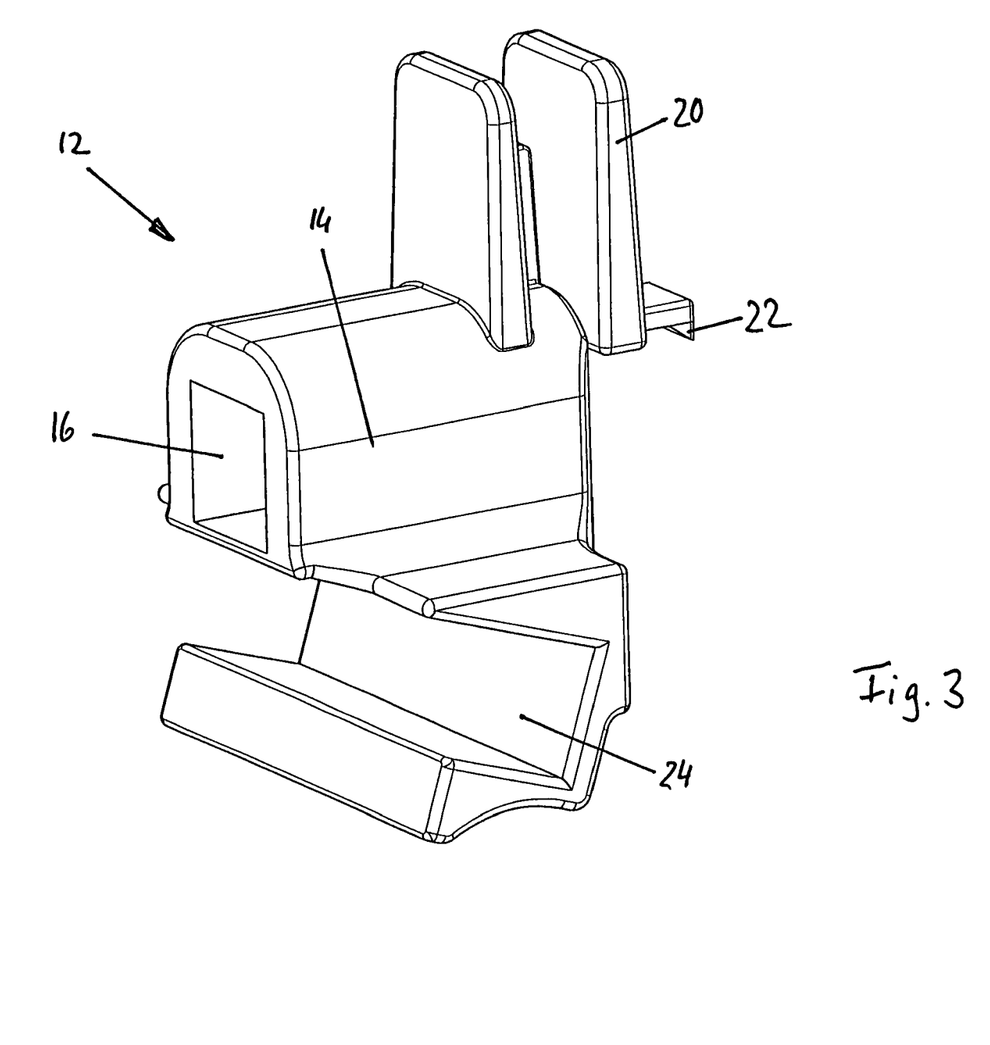
FIG. 3 shows a jaw of the instrument.
Figure 4:
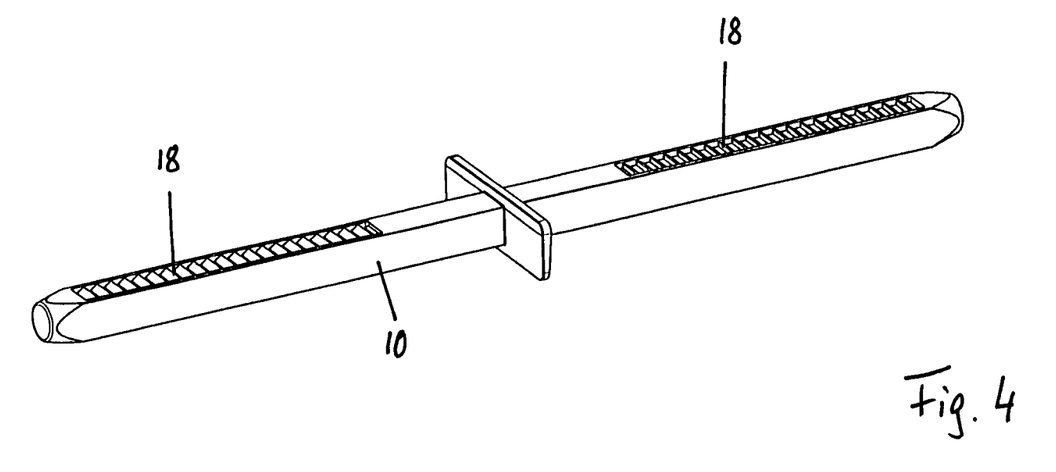
FIG. 4 shows the guide bar of the instrument.

Beneath the pusher 14, each of the jaws comprises a receptacle 24. The receptacle 24 has the shape of a continuous groove running transverse to the guide bar 10, the groove being open toward the front side of the jaw 12. The receptacle 24 has a rectangular cross-section, for example, wherein the rectangular cross-section is slightly tilted relative to the plane perpendicular to the guide bar 10. The tilt angle can be about 30°, for example. Due to this tilt, the open front side of the receptacle 24 is positioned higher, i.e., closer to the guide bar 10 than the closed base of the receptacle 24. The width of the receptacle 24 transverse to the guide bar 10 corresponds approximately to the width of the pusher 14 or is slightly wider than said pusher 14.

Figure 2:
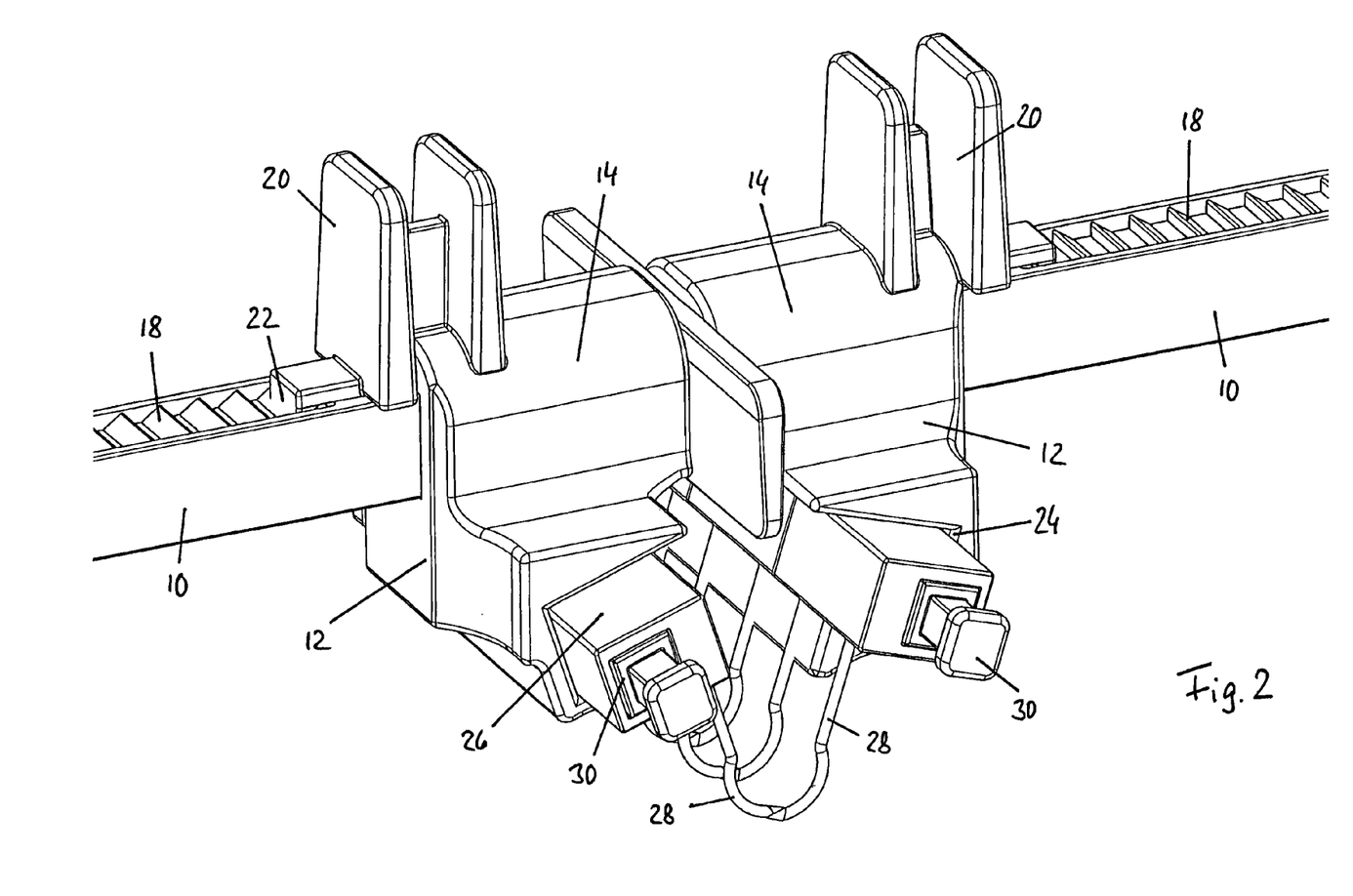
FIG. 2 shows a partial view of this instrument without the fixing element.
Figure 6:
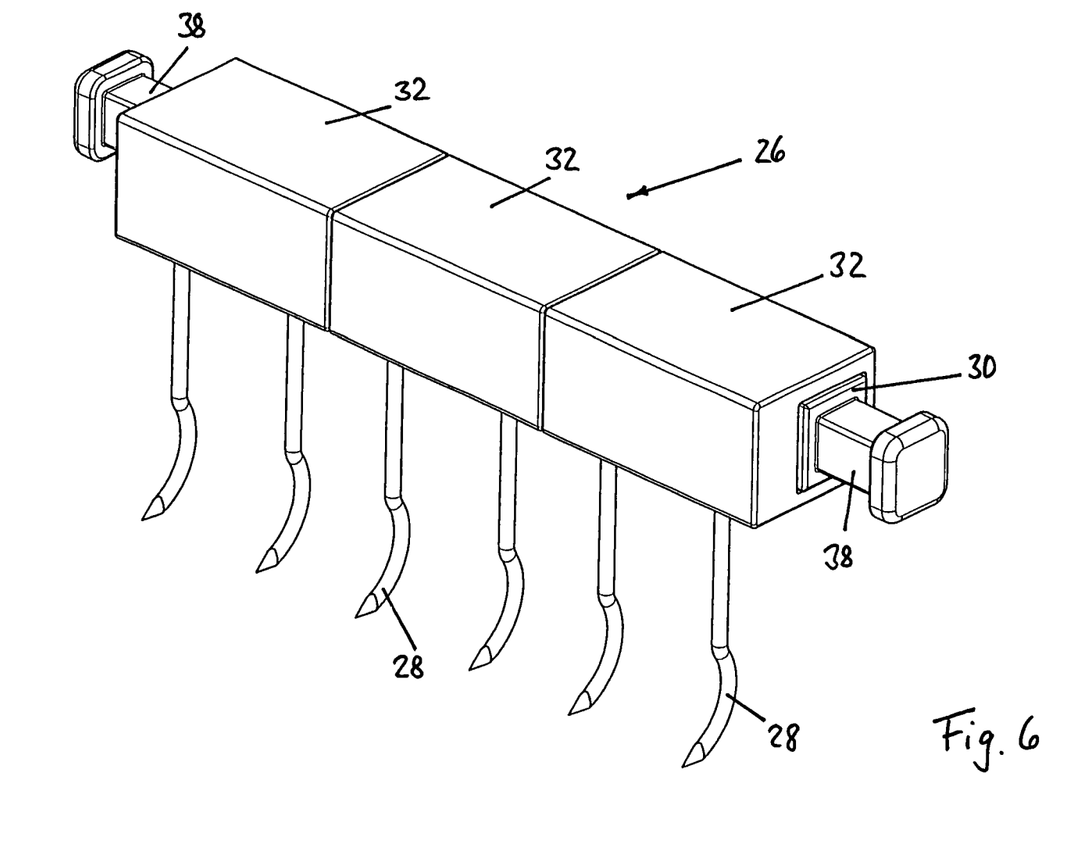
FIG. 6 shows barb modules disposed on a carrier.

Into the receptacle 24, a carrier 26 can be placed on which the barbs 28 are disposed that can be pierced into the skin. The carrier 26 sits in the receptacle 24 with a cross-section that corresponds to the inner cross section of the receptacle 24 so that the carrier 26 with the barbs 28 is non-rotatably held in the jaws 12. The barbs 28 are disposed on the carrier 26 such that when the carrier 26 is inserted, the barbs 28 are tilted toward the plane perpendicular to the guide bar 10, for example by a tilt angle of about 30°.

As can be seen from FIG. 6, for example, in the exemplary embodiment shown, the carrier 26 comprises a bolt 30 with a non-round cross-section. Each of the barbs 28 is disposed in barb modules 32 that can be axially pushed onto the bolts 30 and that are held non-rotatably on the bolt 30 by virtue of the non-round cross-section of the bolt 30. Each barb module 32 holds one or a few barbs 28, two barbs 28 each in the exemplary embodiment shown. The length of the bolts 30 is preferably larger than the length of the receptacles 24 in the transverse direction so that the carriers 26 cover a larger width than the jaws 12. The number of barb modules 32 attached onto the bolt 30, and the distances thereof from one another on the bolt 30 can be freely selected.

A fixing element 34 can be attached at least at one free end of the carrier 26 on each of the bolts 30, and preferably at both free ends in the exemplary embodiment shown.

Figure 5:
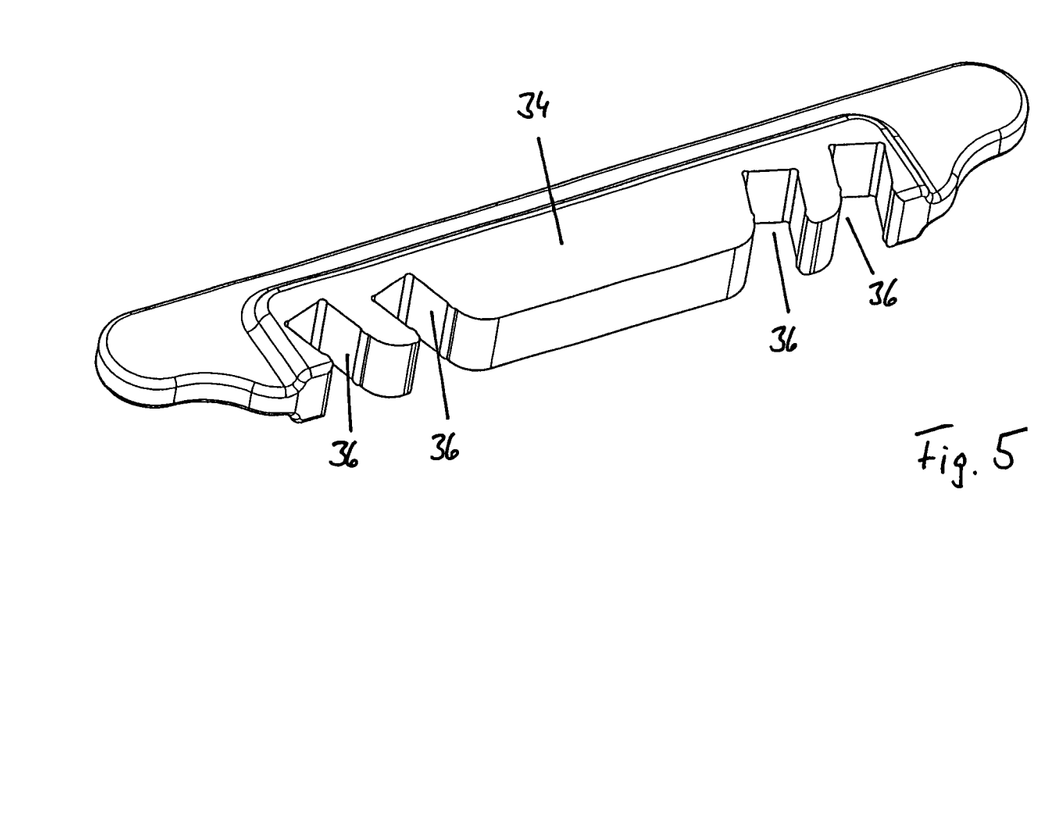
FIG. 5 shows a fixing element.

The fixing element 34 has the shape of a flat disc, the plane of which is perpendicular to the transverse axis of the carrier 26, in particular perpendicular to the axis of the bolts 30. The height of the disc is preferably selected such that when the fixing element 34 is attached, the barbs 28 protrude downward beyond the periphery of the fixing element 34, whereas the upper edge of the fixing element protrudes as little as possible beyond the jaws. The length of the fixing elements 34 in the longitudinal direction of the guide bar 10 is selected such that the fixing element 34 can be attached at least onto the two carriers 26 that are received in jaws 12 that adjoin one another on the guide bar 10.

Figure 7:
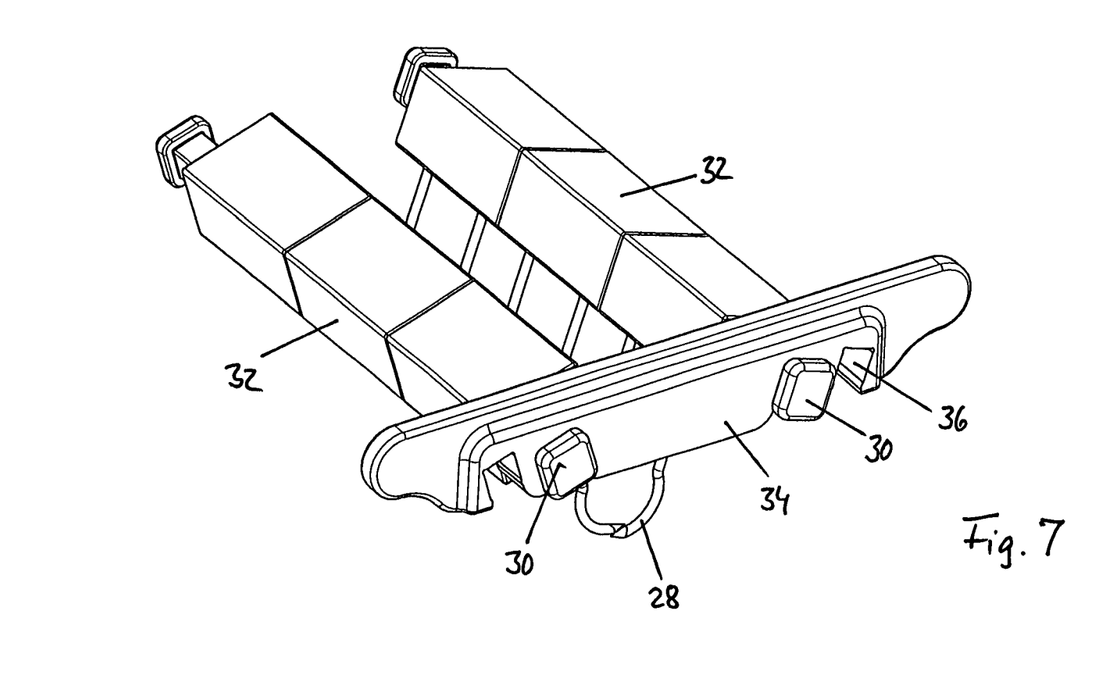
FIG. 7 shows two carriers fixed by means of the fixing element.

In an embodiment shown in particular in FIGS. 5 to 7, the disc of the fixing element 34 comprises edge notches 36 at the lower edge of the fixing element, by means of which notches the fixing element 34 can be attached from above onto the free ends of the bolts 30. In the process of this, the edge notches 36 engage around the free ends of the bolts 30 in a section 38 of reduced cross-sectional area. Thereby, the fixing elements 34 are securely held on the bolts 30 against shifting in the axial direction of the bolts 30. The cross-section of the sections 38 comprises parallel surfaces that are chamfered at the tilt angle of the carrier 26, which parallel surfaces are allocated correspondingly chamfered parallel surfaces of the edge notches 36. In this way, the installed fixing element 34 holds the bolts 30 and thereby the carriers 26 securely against being rotated about the axis of the bolt 30.

The use of the instrument according to the invention is described below.

Figure 1:
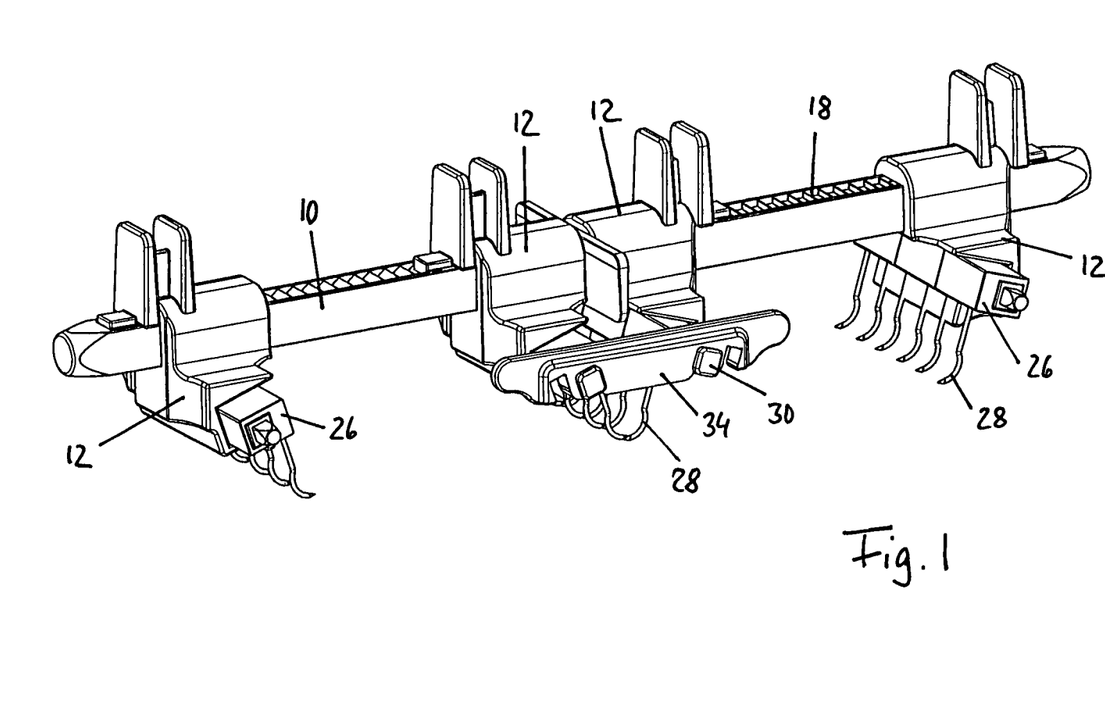
FIG. 1 shows an instrument comprising a fixing element placed thereon.

To close a large-area skin defect, the skin expander is used as shown in FIGS. 1 and 2, for example. In each case one carrier 26 is anchored in the skin at the opposite edges of the wound. To this end, in particular bolts 30, having a suitable length and an appropriately selected number of barb modules 32, are anchored in place by piercing the barbs 28 into the skin. Then, the skin expander is set in place, wherein two jaws 12 are disposed on the guide bar 10 in such a way that the receptacles 24 thereof face one another. First of all, the jaws 12 are positioned on the guide bar 10 at a large mutual distance so that each of the carriers 26 anchored at the edges of the wound, which are spaced far apart from one another, can be placed into the respective receptacle 24 of the two jaws 12. Then, the jaws 12 are moved toward one another on the guide bar 10. This pulls the edges of the wound together, wherein the skin areas situated behind the barbs 28 in the direction of tension are stretched. Since the carriers 26 and the barbs 28 are held in the respective receptacle 24 in a non-rotatable manner, the elastic force of the skin cannot tilt the barbs 28 backward, and the carriers 26 cannot be lifted out of the receptacles 24. Also, since the barbs 28 are tilted at a tilt angle of about 30°, the tips of the barbs 28 being directed forward, it is also ensured that the barbs 18 cannot be pulled out of the skin of the edge of the wound. While the two jaws 12 are moved toward one another, the latching teeth 22 slide in each case over the toothed latching arrangement 18, while the latching of the latching teeth 22 into the toothed latching arrangement 18 prevents the jaws 12 from being pulled back due to the elastic tensile stress of the skin.

As soon as the two jaws 12 are fully moved toward one another, the opposing tips of the barbs 28 slightly overlap, for example by about 3 mm, as is shown in FIG. 2. In this position of the jaws 12, the fixing element 34 is now attached onto the overhanging free ends of the bolts 30, as is shown in FIG. 1. The fixing element 34 now firmly holds the two carriers 26 positioned at their distance from one another. Preferably, two fixing elements 34 are used, wherein on both of the ends of the bolts, in each case one fixing element 34 is placed. This ensures that the bolts 30 are held positioned along the entire length thereof. The elastic tensile force of the stretched and tensioned skin pulls the bolts 30, which are in an inclined position, into the inclined edge notches 36 so that the bolts cannot come free from the fixing element 34. As soon as the carriers 26 are fixed in position and at their distance by the fixing elements 34, the jaws 12 are moved away from one another so that the latching teeth 22 can be lifted out of the toothed latching arrangement 18 by means of the latch lever 20. When the jaws 12 are moved apart, the fixed carriers 26 are freed from the receptacles 24 so that the skin expander can be removed. The carriers 26 with the barbs 28 (FIG. 7), which are held together by the fixing elements 34, hold the edges of the wound against one another so that stitching of the edges of the wound is not required.

In the exemplary embodiment shown, the fixing element 34 comprises in each case two edge notches 36 for each of the carriers 26, as is shown in particular in FIG. 5. This makes it possible to fix the carriers 26 and barbs 28 at different mutual distances so that the abutting edges of the wound can be optimally adjusted.

As shown in FIG. 1, other jaws 12 can be disposed on the guide bar 10 behind the two jaws 12 that are anchored in the edges of the wound, the other jaws holding carriers that are anchored by means of barbs 28 in the skin area to be stretched at a distance from the respective edge of the wound. This makes it possible to more evenly distribute the tensile force acting on the skin over a larger skin area, as is known from EP 2 120 767 B1, for example.

If the skin defect is so large that it cannot be closed through skin-stretching in a single step, it is also possible to use fixing elements 34, the edge notches 36 of which have a larger distance in the direction of tension. The jaws 12 are then each moved toward one another step by step, wherein in each step, the skin at the edges of the wound is stretched by a maximum allowable amount. After each stretching step, the jaws 12 can be fixed in their respective position by means of suitably long fixing elements 34. The skin expander can then be removed until it is used again for the next stretching step. In the meantime, the surface of the wound that remains open can be covered by a vacuum seal together with the carriers 26 that are anchored in the edges of the wound and fixed by means of the fixing elements 34.

Figure 8:
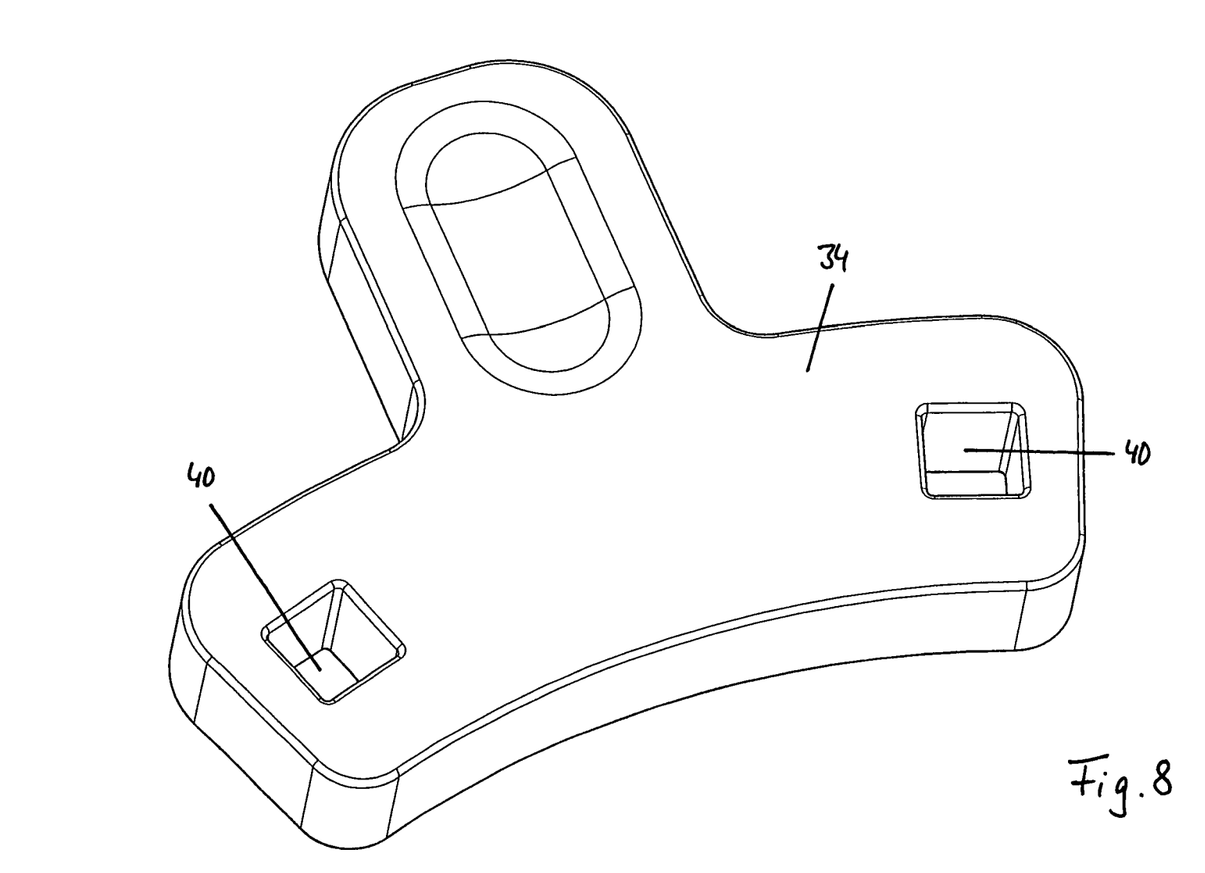
FIG. 8 shows the fixing element in a second embodiment.
Figure 9:
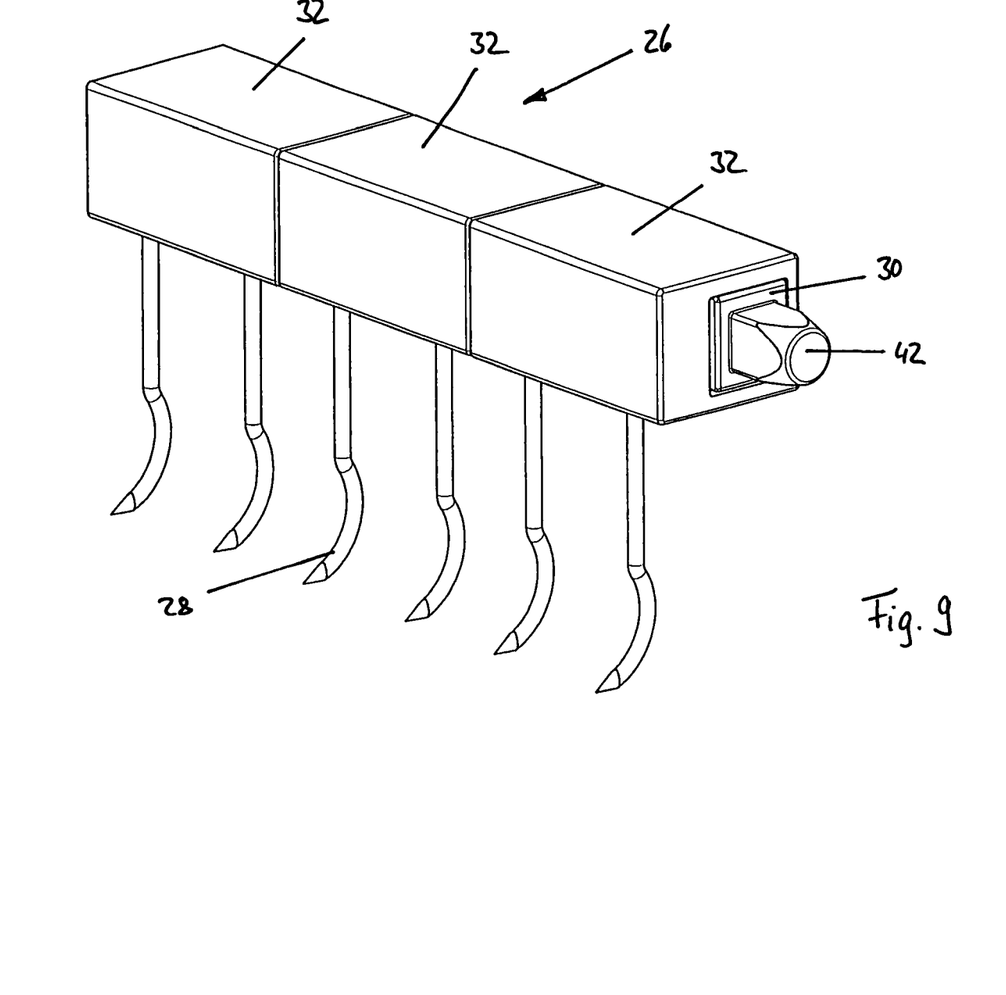
FIG. 9 shows barb modules disposed on a carrier in the second embodiment.
Figure 10:
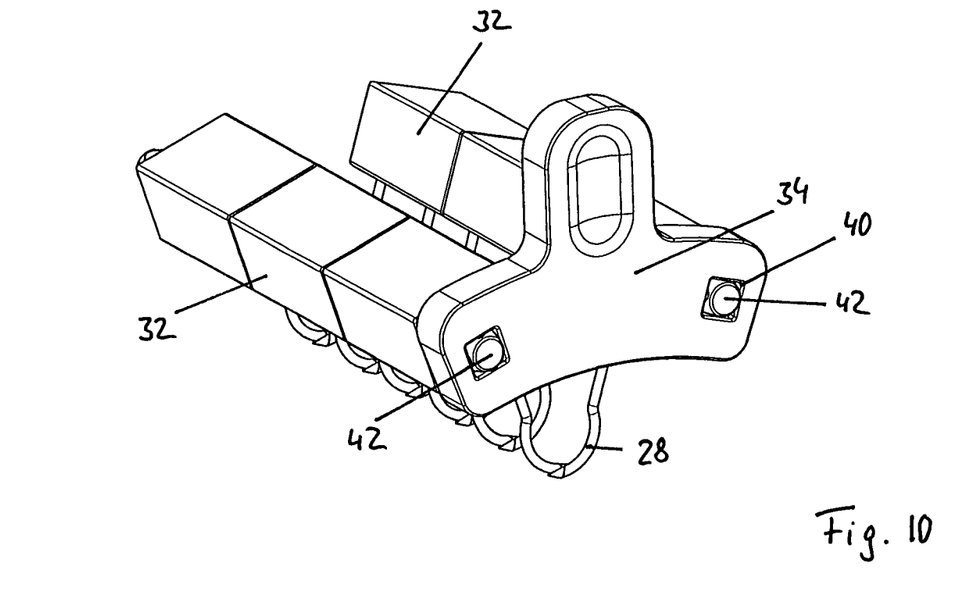
FIG. 10 shows two carriers fixed by means of the fixing element in the second embodiment.

An alternative second embodiment of the fixing element 34 is shown in FIGS. 8 to 10. In this embodiment, the fixing element 34 is also designed as a flat disc. Instead of edge notches, the flat disc of the fixing element 34 comprises openings 40 in the surface of the fixing element 34, by means of which openings the fixing element 34 can be placed axially onto the free ends of the carrier 26, i.e., in particular onto the free ends 42 of the bolts 30. In this embodiment, it is also possible to design the openings 40 of the fixing element 34 as slots running parallel to the guide bar 10. The free ends 42 of the carriers 26 that extend through the openings 40 can be moved within these slots in order to re-adjust the distance between the carriers 26 anchored in the two edges of the wound. In order to fix the carriers 26 in the respective readjustment position, a toothed latching arrangement is disposed in each of the slots of the fixing elements 34, which latching arrangement enables moving the carriers 26 toward one another, but which prevents the carriers 26 from being pulled back by the elastic tensile force of the skin. In particular, this embodiment enables readjustment of the carriers 26 anchored in the skin when the elastic restoring tension of the skin decreases as a result of the stretched skin.

REFERENCE LIST

10 Guide bar
12 Jaws
14 Pusher
16 Opening
18 Toothed latching arrangement
20 Latch lever
22 Latching tooth
24 Receptacle
26 Carrier
28 Barbs
30 Bolts
32 Barb modules
34 Fixing element
36 Edge notches
38 Section
40 Openings
42 Free ends

The invention claimed is:

1. An instrument for stretching skin for closing a wound, comprising:
    a skin expander, having at least two jaws mechanically adjustable relative to each other in a tension direction on the skin expander, having barbs that are associated with the jaws and configured to be anchored in the skin in an area of the wound edge;
    wherein a tensile force is exerted on the skin via the barbs by adjusting a distance between the at least two jaws, the tensile force stretching the skin and drawing the edges of the wound toward each other,
    wherein at least one barb of the barbs is disposed on a carrier of a plurality of carriers extending transverse to the tension direction, wherein the plurality of carriers are releasably mounted on the at least two jaws,
    wherein the plurality of carriers can be fixed in position relative to each other by a fixing element,
    wherein each carrier of the plurality of carriers further comprises a bolt with a free end,
    wherein the fixing element can be attached onto the free end of the bolt of at least two carriers of the plurality of carriers, and
    wherein the fixing element has a disc shape that comprises edge notches and can be attached onto the free end of the bolt of at least two carriers of the plurality of carriers to maintain the distance between the at least two jaws.

2. The instrument according to claim 1, wherein at least one barb of the barbs is disposed on a barb module and the barb module is attached in a non-rotatable manner onto the bolt, wherein each bolt has a non-round cross section.

3. The instrument according to claim 1, wherein each carrier of the plurality of carriers can be placed in a non-rotatable manner into a receptacle of each jaw of the at least two jaws, wherein each receptacle runs transverse to the direction of the tension direction and each receptacle having an opening in the direction of the tension direction.

4. The instrument according to claim 1, wherein at least two carriers of the plurality of carriers can be fixed at adjustable mutual distances by the fixing element.

5. The instrument according to claim 1, wherein the fixing element comprises edge notches which are offset from one another in the direction of the tension direction and the fixing element can be selectively attached onto the bolt of at least two carriers of the plurality of carriers with the edge notches.

6. An instrument for stretching skin for closing a wound, comprising:
- a skin expander, having at least two jaws mechanically adjustable relative to each other in a tension direction on the skin expander, having barbs that are associated with the at least two jaws and configured to be anchored in the skin in an area of the wound edge;
- wherein a tensile force is exerted on the skin via the barbs by adjusting a distance between the at least two jaws, the tensile force stretching the skin and drawing the edges of the wound toward each other,
- wherein at least one barb of the barbs is disposed on a carrier of a plurality of carriers extending transverse to the tension direction, wherein the plurality of carriers are releasably mounted on the at least two jaws,
- wherein the plurality of carriers can be fixed in position relative to each other by a fixing element,
- wherein each carrier of the plurality of carriers further comprises a bolt with a free end,
- wherein the fixing element can be attached onto the free end of the bolt of at least two carriers of the plurality of carriers, and
- wherein the fixing element has a disc shape, wherein the fixing element further comprises openings and wherein the openings can be attached onto the bolt of at least two carriers of the plurality of carriers.

7. The instrument according to claim 6, wherein each of the openings comprise a latching that runs in the direction of the tension direction, and the bolt of at least two carriers of the plurality of carriers can be adjustably latched into this latching in the direction of the tension direction.

8. The instrument according to claim 6, wherein at least one barb of the barbs is disposed on a barb module and the barb module is attached in a non-rotatable manner onto the bolt which has a non-round cross section.

9. The instrument according to claim 6, wherein one carrier of the plurality of carriers can be placed in a non-rotatable manner into a receptacle of each jaw of the at least two jaws, wherein each receptacle runs transverse to the direction of the tension direction and is open in the direction of the tension direction.

10. The instrument according to claim 6, wherein at least two carriers of the plurality of carriers can be fixed at adjustable mutual distances by the fixing element.

* * * * *